(12) United States Patent
Mashuga et al.

(10) Patent No.: US 11,307,157 B2
(45) Date of Patent: Apr. 19, 2022

(54) METHOD AND APPARATUS FOR MINIMUM IGNITION ENERGY TESTING

(71) Applicant: The Texas A&M University System, College Station, TX (US)

(72) Inventors: Chad Mashuga, Manvel, TX (US); Purvali Chaudhari, College Station, TX (US)

(73) Assignee: The Texas A&M University System, College Station, TX (US)

( * ) Notice: Subject to any disclaimer, the term of this patent is extended or adjusted under 35 U.S.C. 154(b) by 357 days.

(21) Appl. No.: 16/467,403

(22) PCT Filed: Dec. 19, 2017

(86) PCT No.: PCT/US2017/067259
§ 371 (c)(1),
(2) Date: Jun. 6, 2019

(87) PCT Pub. No.: WO2018/118889
PCT Pub. Date: Jun. 28, 2018

(65) Prior Publication Data
US 2020/0049637 A1    Feb. 13, 2020

Related U.S. Application Data

(60) Provisional application No. 62/567,595, filed on Oct. 3, 2017, provisional application No. 62/436,247, filed on Dec. 19, 2016.

(51) Int. Cl.
*G01N 25/54* (2006.01)
*G01N 33/22* (2006.01)
*G01N 33/00* (2006.01)

(52) U.S. Cl.
CPC ........... *G01N 25/54* (2013.01); *G01N 33/227* (2013.01); *G01N 2033/0091* (2013.01)

(58) Field of Classification Search
CPC ................ G01N 25/54; G01N 33/227; G01N 2033/0091
See application file for complete search history.

(56) References Cited

U.S. PATENT DOCUMENTS 3,545,252 A    12/1970 Springfield et al.
3,768,313 A    10/1973 Johansson et al.
(Continued)

FOREIGN PATENT DOCUMENTS

GB        728161    *  4/1955

OTHER PUBLICATIONS

Ackroyd, Graham et al.; "The effect of reduced oxygen levels on the electrostatic ignition sensitivity of dusts"; Journal Physics: Conference Series 301; 2011; 5 pages.
(Continued)

*Primary Examiner* — Daniel S Larkin
(74) *Attorney, Agent, or Firm* — Winstead PC

(57) ABSTRACT

A minimum-ignition-energy testing apparatus includes a combustion tube and a bottom assembly coupled to a lower end of the combustion tube. A top assembly is coupled to an upper end of the combustion tube. The top assembly includes a first sparge plate coupled to the top base plate. The first sparge plate has a first aperture formed therein. The top assembly also includes a second sparge plate coupled to the first sparge plate. The second sparge plate has formed therein a second aperture that aligns in registry with the first aperture. A channel is formed in the second sparge plate about a perimeter of the third aperture. The channel has a plurality of holes disposed therein that are formed through a thickness of the second sparge plate. A tube is formed through in the second sparge plate, the tube fluidly coupling the channel to a gas source.

19 Claims, 6 Drawing Sheets

(56) References Cited

U.S. PATENT DOCUMENTS

| | | | |
|---|---|---|---|
| 4,140,004 | A | 2/1979 | Smith et al. |
| 5,246,667 | A | 9/1993 | Hemzy et al. |
| 2006/0133445 | A1 | 6/2006 | Lyon |
| 2015/0276701 | A1 | 10/2015 | Farrell et al. |

OTHER PUBLICATIONS

ASTM International; "Standard Test Method for Minimum Ignition Energy of a Dust Cloud in Air"; E2019-03; 2007; 8 pages.

Beckman Coulter, Inc.; "LS 13 320 Laser Diffraction Particle Size Analyzer"; Oct. 2011; 246 pages.

Abbasi, Tasneem et al.; "Dust explosions-Cases, causes, consequences, and control"; Journal of Hazardous Materials; 140; 2007; pp. 7-44.

Choi, Kwangseok et al.; "Experimental study on the influence of the nitrogen concentration in the air on the minimum ignition energies of combustible powders due to electrostatic discharges"; Journal of Loss Prevention in the Process Industries; 34; 2015; pp. 163-166.

Cesana, Christoph et al.; "MIKE—Manual"; Cesana-AG; Dec. 4, 2016; 34 pages.

Eckhoff, Rolf K.; "Partial inerting—an additional degree of freedom in dust explosion protection"; Journal of Loss Prevention in the Process Industries; 17; 2004; pp. 187-193.

Kühner, A.; "Final Report. Calibration Round-Robin test for the determination of the explosion characteristics of dusts"; CaRo15; 2015; 2 pages.

Reinhardt, Hans-Jürgen et al.; "Inerting in the chemical industry."; The Linde Group; 56 pages.

Young, Lee W., International Search Report for PCT/US2017/067259, dated Mar. 8, 2018, 1 page.

\* cited by examiner

METHOD AND APPARATUS FOR MINIMUM IGNITION ENERGY TESTING

CROSS-REFERENCE TO RELATED APPLICATIONS

The present application claims priority to U.S. Provisional Patent Application No. 62/436,247, filed on Dec. 19, 2016 and U.S. Provisional Patent Application No. 62/567,595, filed on Oct. 3, 2017. U.S. Provisional Patent Application No. 62/436,247 and U.S. Provisional Patent Application No. 62/567,595 are each incorporated herein by reference.

BACKGROUND

Technical Field

The present application relates generally to testing of process byproducts and more particularly, but not by way of limitation, to minimum-ignition-energy testing of dust using partial inerting of the dust, and hybrid dust-flammable gas testing.

History of the Related Art

This section provides background information to facilitate a better understanding of the various aspects of the disclosure. It should be understood that the statements in this section of this document are to be read in this light, and not as admissions of prior art.

In process industries, explosions from process byproducts, such as dust, can present an unexpected hazard to the facilities. Minimum-Ignition Energy ("MIE") of a dust is the minimum amount of energy required for ignition of the dust at conditions of ambient temperature and pressure. It is important to accurately determine the MIE of combustible dust because MIE gives an estimate of the ignition sources that need to be eliminated in facilities handling such dusts. Inerting of combustible gas using an inert gas, such as nitrogen, is one of the most viable methods of maintaining safety standards in an industry. Inerting in industries can be carried out for reactors, grinding and mixing plants, tank farm vessels, silos, filling facilities, and dryers.

Amongst various dust explosion mitigation techniques, partial inerting is an important technique having wide application potential in industry. Partial inerting involves reducing the oxygen content by replacing it with an inert gas, such as nitrogen, which causes the MIE of the dust to increase. The most common inert gas used in industries is nitrogen. Many times complete inerting of a facility can be unnecessary, expensive, and amount to a waste of resources. It has been observed that, for many dusts, inerting in even small amounts can significantly increase the MIE and render the dust safer. Therefore, partial inerting provides a simpler alternative to complete inerting.

SUMMARY

The present application relates generally to testing of process byproducts and more particularly, but not by way of limitation to minimum-ignition-energy testing of dust using partial inerting of the dust, and testing of dust in the presence of a flammable gas or vapor, also known as hybrid MIE dust testing. In a first aspect, the present disclosure relates to a minimum-ignition-energy testing apparatus. The minimum-ignition-energy testing apparatus includes a combustion tube and a bottom assembly coupled to a lower end of the combustion tube. A top assembly is coupled to an upper end of the combustion tube. The top assembly includes a first sparge plate coupled to the top base plate. The first sparge plate has a first aperture formed therein. The top assembly also includes a second sparge plate coupled to the first sparge plate. The second sparge plate has formed therein a second aperture that aligns in registry with the first aperture. A channel is formed in the second sparge plate about a perimeter of the third aperture. The channel has a plurality of holes disposed therein that are formed through a thickness of the second sparge plate. A tube is formed through in the second sparge plate, the tube fluidly coupling the channel to a gas source.

In another aspect, the present disclosure relates to a minimum-ignition-energy testing method. The minimum-ignition-energy testing method includes placing a material on a bottom assembly of a minimum-ignition-energy testing apparatus and enclosing the material in a combustion tube. An inerting gas or a gas containing fuel is provided to a top assembly coupled to the combustion tube to purge the combustion tube. The material is dispersed into the combustion tube and an ignition energy is applied to the combustion tube.

In another aspect, the present disclosure relates to a top assembly for use with a combustion tube. The top assembly includes a top base plate having a first aperture formed therein and a flapper plate pivotably coupled thereto. The flapper plate covers the first aperture. The top assembly also includes a first sparge plate coupled to the top base plate, the first sparge plate includes a second aperture formed therein that aligns in registry with the first aperture. The top assembly also includes a second sparge plate coupled the first sparge plate. The second sparge plate includes formed therein a second aperture that aligns in registry with the first aperture and with the second aperture. The top assembly also includes a channel formed in the second sparge plate about a perimeter of the third aperture. The channel includes a plurality of holes disposed therein. The holes are formed through a thickness of the second sparge plate. A tube is formed through in the second sparge plate, the tube fluidly coupling the channel to a gas source.

This summary is provided to introduce a selection of concepts that are further described below in the detailed description. This summary is not intended to identify key or essential features of the claimed subject matter, nor is it to be used as an aid in limiting the scope of the claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Various embodiments will now be described more fully with reference to the accompanying drawings. The disclosure may, however, be embodied in many different forms and should not be construed as limited to the embodiments set forth herein.

Figure 1:
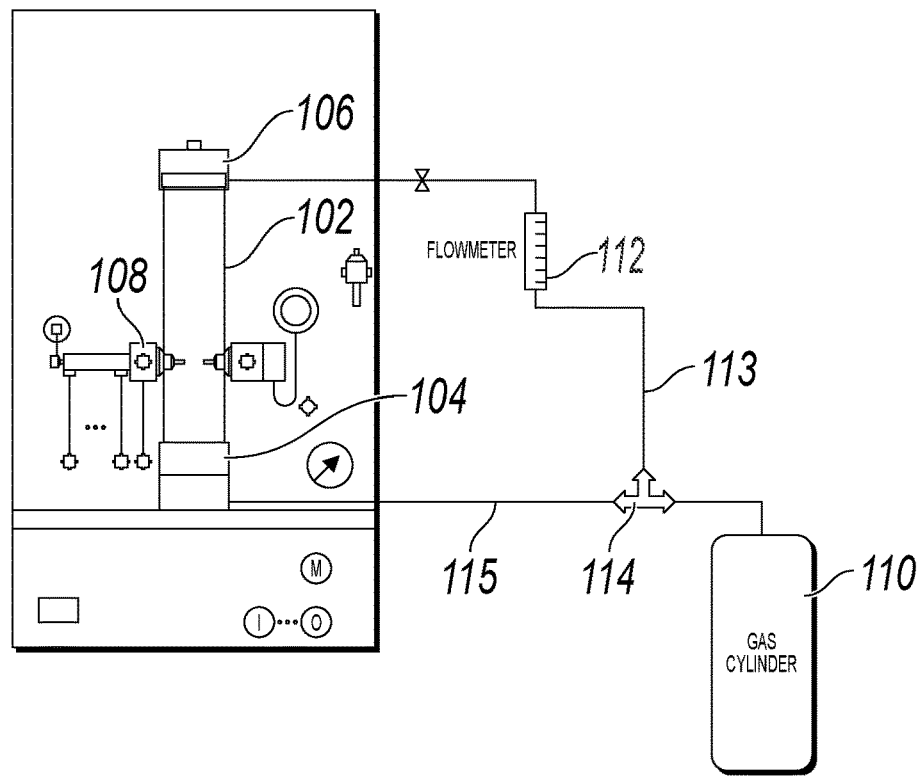
FIG. 1 is a schematic diagram of a minimum-ignition-energy apparatus in accordance with an exemplary embodiment.

FIG. 1 is a schematic diagram of a minimum-ignition-energy apparatus 100. The minimum-ignition-energy apparatus 100 includes a combustion tube 102. The combustion tube 102 has a volume of approximately 1.2 L; however, in other embodiments, various other sizes could be utilized according to design requirements. A bottom assembly 104 and a top assembly 106 are coupled to a lower and upper end of the combustion tube 102, respectively. An ignition device 108 is coupled to the combustion tube 102 in such a manner as to expose an interior of the combustion tube 102 to a source of ignition. In various embodiments, the ignition device 108 is, for example, a spark ignition device. In a typical embodiment, energy generated by the ignition device 108 is in a range of approximately 1 mJ to approximately 1000 mJ. The ignition device 108 is powered by alternating-current or direct-current electrical power; however, in other embodiments, other types of power sources could be utilized.

Still referring to FIG. 1, the bottom assembly 104 and the top assembly 106 are fluidly coupled to a gas source 110. By way of example, the gas source 110 is illustrated in FIG. 1 as a gas cylinder; however, in other embodiments, the gas source 110 could be any source of compressed gas such as, for example, a laboratory or building gas supply. As illustrated in FIG. 1, one or more flow meters 112 are utilized to measure a flow of gas to at least one of the bottom assembly 104 and the top assembly 106. A valve 114 is utilized to divide flow of gas between the bottom assembly 104 and the top assembly 106. In a typical embodiment, the valve 114 is a T-shaped valve that divides flow of gas from the gas source 110 into a first fluid stream 113, coupled to the top assembly 106, and a second fluid stream 115, coupled to the bottom assembly 104.

Figure 2:
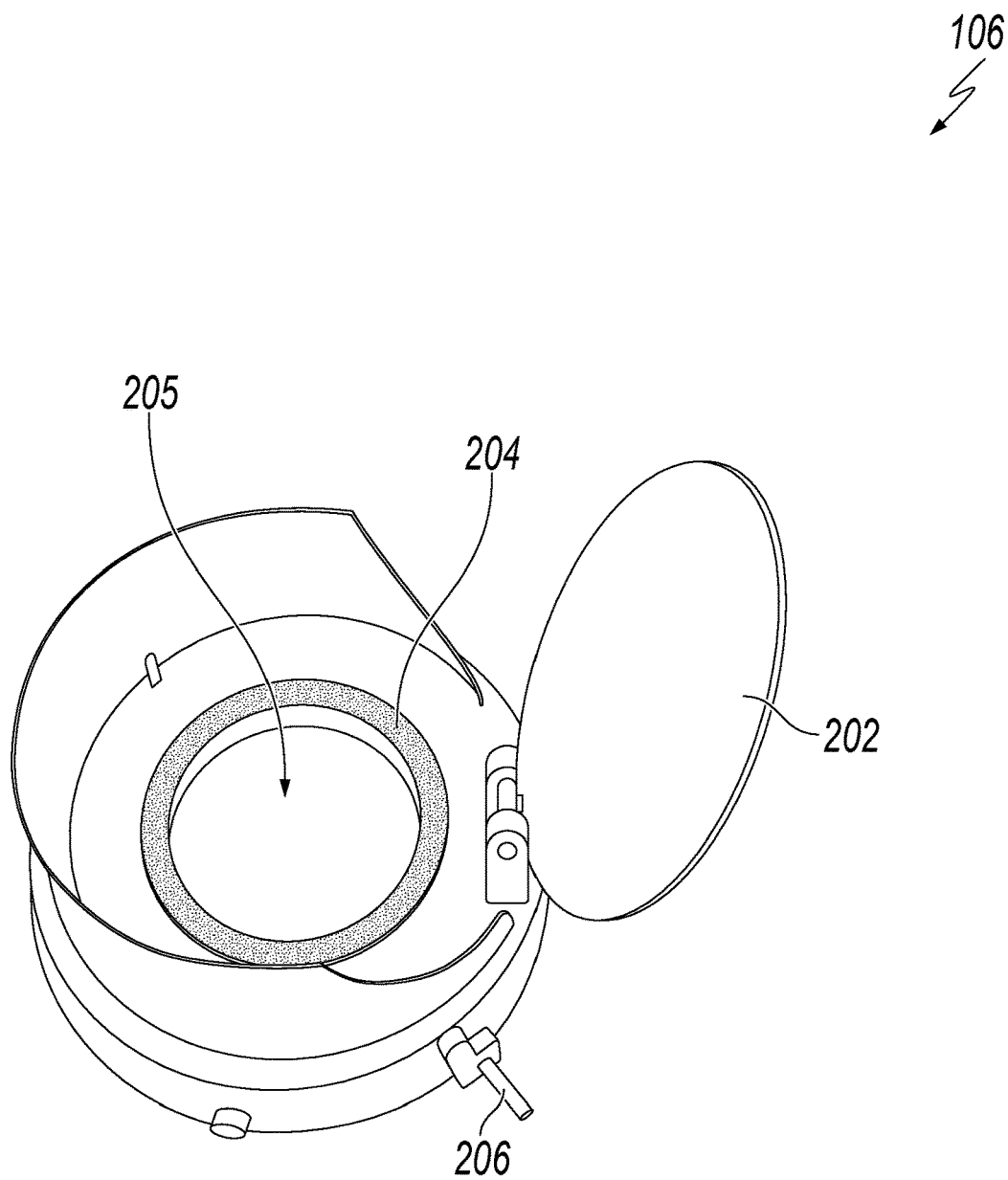
FIG. 2 is a perspective view of the top assembly of the minimum-ignition-energy apparatus in accordance with an exemplary embodiment.

FIG. 2 is a perspective view of the top assembly 106 of the minimum-ignition-energy apparatus 100. The top assembly includes a flapper plate 202 that is hingedly movable between a closed position and an open position. A foam seal 204 is positioned around a perimeter of an aperture 205 formed in the top assembly 106. The foam seal 204 seals the flapper plate 202 when the flapper plate 202 is in the closed position, thereby preventing leakage of ambient air into the combustion tube 102 through the aperture. The flapper plate 202 moves from the closed position to the open position responsive to increased pressure within the combustion tube 102 resulting from combustion within the combustion tube 102. The top assembly 106 also includes a fluid connection 206. During operation, the fluid connection 206 is coupled to the gas source 110 via the valve 114.

Figure 3:
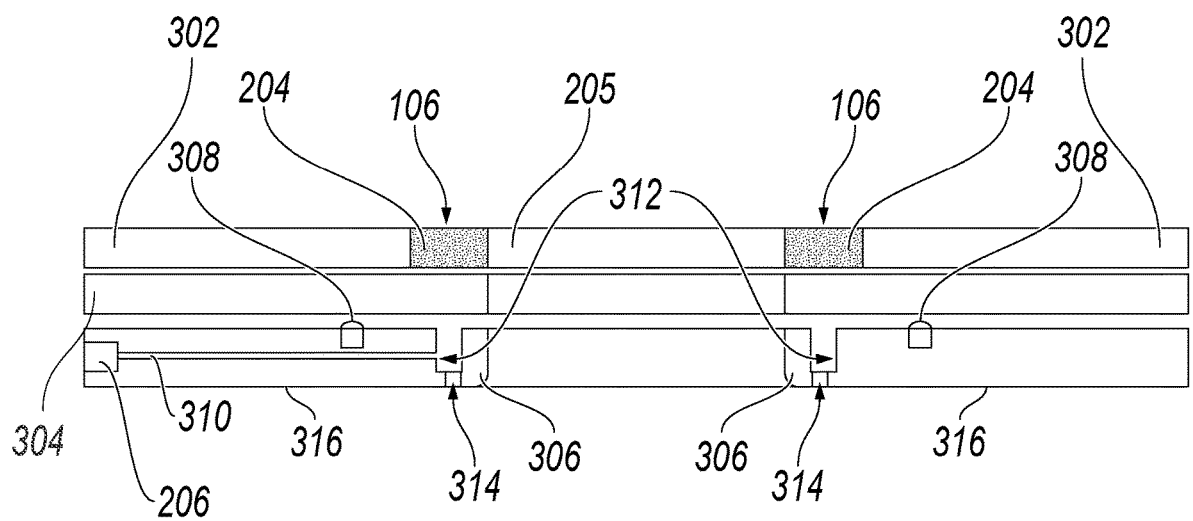
FIG. 3 is a side cross-sectional view of a top assembly of the minimum-ignition-energy apparatus with a flapper plate removed in accordance with an exemplary embodiment.

FIG. 3 is a side cross-sectional view of the top assembly 106 of the minimum ignition energy apparatus 100 with the flapper plate 202 removed. The top assembly 106 includes a top base plate 302. The top base plate 302 is coupled to a first sparge plate 304 and the first sparge plate 304 is coupled to a second sparge plate 306. The first sparge plate 304 and the second sparge plate 306 are formed of, for example, 316 stainless steel; however, in other embodiments, devices utilizing principles of the present disclosure may include sparge plates from any appropriate material. A tube 310 is formed in the second sparge plate 306 and connects the fluid connection 206 to a channel 312 formed in the second sparge plate 306. The tube 310 has a diameter of approximately $\frac{1}{16}$ inch; however, in other embodiments, other tube diameters could be utilized. The channel 312 is formed about a perimeter of the aperture 205. During operation, the tube 310 supplies gas from the gas source 110 to the channel 312. A plurality of holes 314 are formed in a bottom surface 316 of the second sparge plate 306. The plurality of holes 314 fluidly couple the channel 312 to an interior of the combustion tube 102. Thus, during operation, gas from the gas source 110 is supplied to the combustion tube 102 via the tube 310 and the channel 312. A seal 308 such as, for example, an O-ring is disposed between the first sparge plate 304 and the second sparge plate 306 outwardly of the channel 312. In a typical embodiment, the seal 308 prevents escape of gas between the first sparge plate 304 and the second sparge plate 306.

Figure 4:
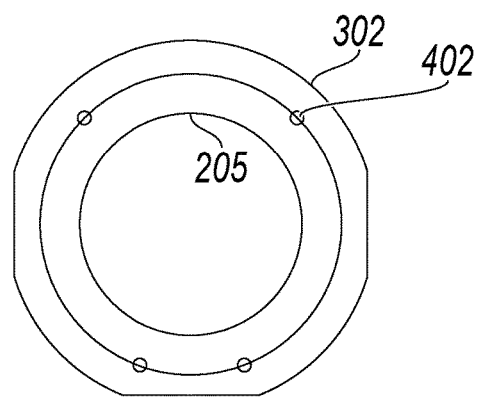
FIG. 4 is a top view of a top base plate in accordance with an exemplary embodiment.
Figure 5:
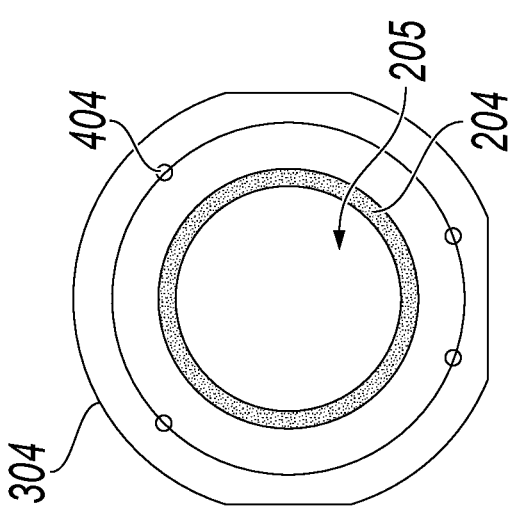
FIG. 5 is a top view of a first sparge plate in accordance with an exemplary embodiment.

FIG. 4 is a top view of the top base plate 302. FIG. 5 is a top view of the first sparge plate 304. Referring to FIGS. 4-5 collectively, the aperture 205 is visible in the top base plate 302 and the first sparge plate 304. A first plurality of mounting holes 402 are formed in the top base plate 302. A second plurality of mounting holes 404 are formed in the first sparge plate 304. When the top base plate 302 and the first sparge plate 304 are assembled, the first plurality of mounting holes 402 and the second plurality of mounting holes 404 align in registry to allow passage of fasteners therethrough.

Figure 6:
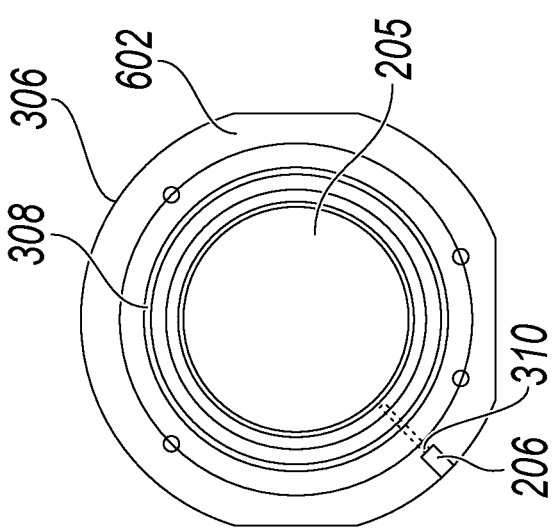
FIG. 6 is a top view of a second sparge plate in accordance with an exemplary embodiment.

FIG. 6 is a top view of a second sparge plate 306. The channel 312 is formed about a perimeter of the aperture 205. The tube 310 is formed through an interior of the second sparge plate 306 and fluidly couples the fluid connection 206 to the channel 312. The seal 308 is disposed on the second sparge plate 306 outwardly of the channel 312. In various embodiments, the seal 308 may be formed in a second channel as illustrated in FIG. 3; however, in other embodiments, the seal 308 may be applied directly to a top surface 602 of the second sparge plate 306.

Figure 7:
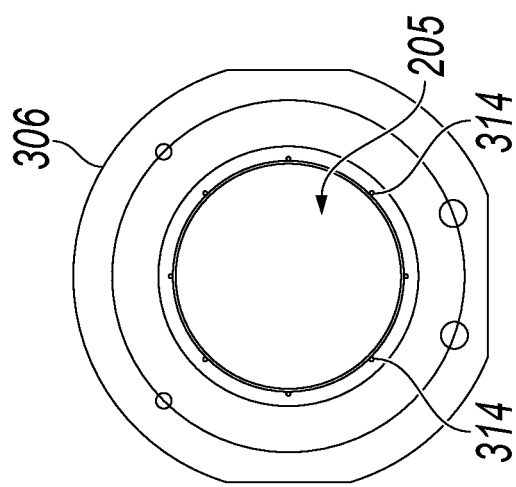
FIG. 7 is a bottom view of a the second sparge plate in accordance with an exemplary embodiment.

FIG. 7 is a bottom view of the second sparge plate 306. The plurality of holes 314 are formed through the second sparge plate 306. The plurality of holes 314 are located so as to be positioned in an interior of the combustion tube 102. The plurality of holes are fluidly coupled to the channel 312. Thus, the plurality of holes 314, the channel 312, and the tube 310 provide a pathway for a gas, from the gas source 110 to access the interior of the combustion tube 102. As illustrated in FIG. 7, the plurality of holes 314 are arranged in an approximately circular arrangement with approximately equi-distant hole spacing; however, in other embodiments, other hole spacing and arrangements could be utilized.

Figure 8:
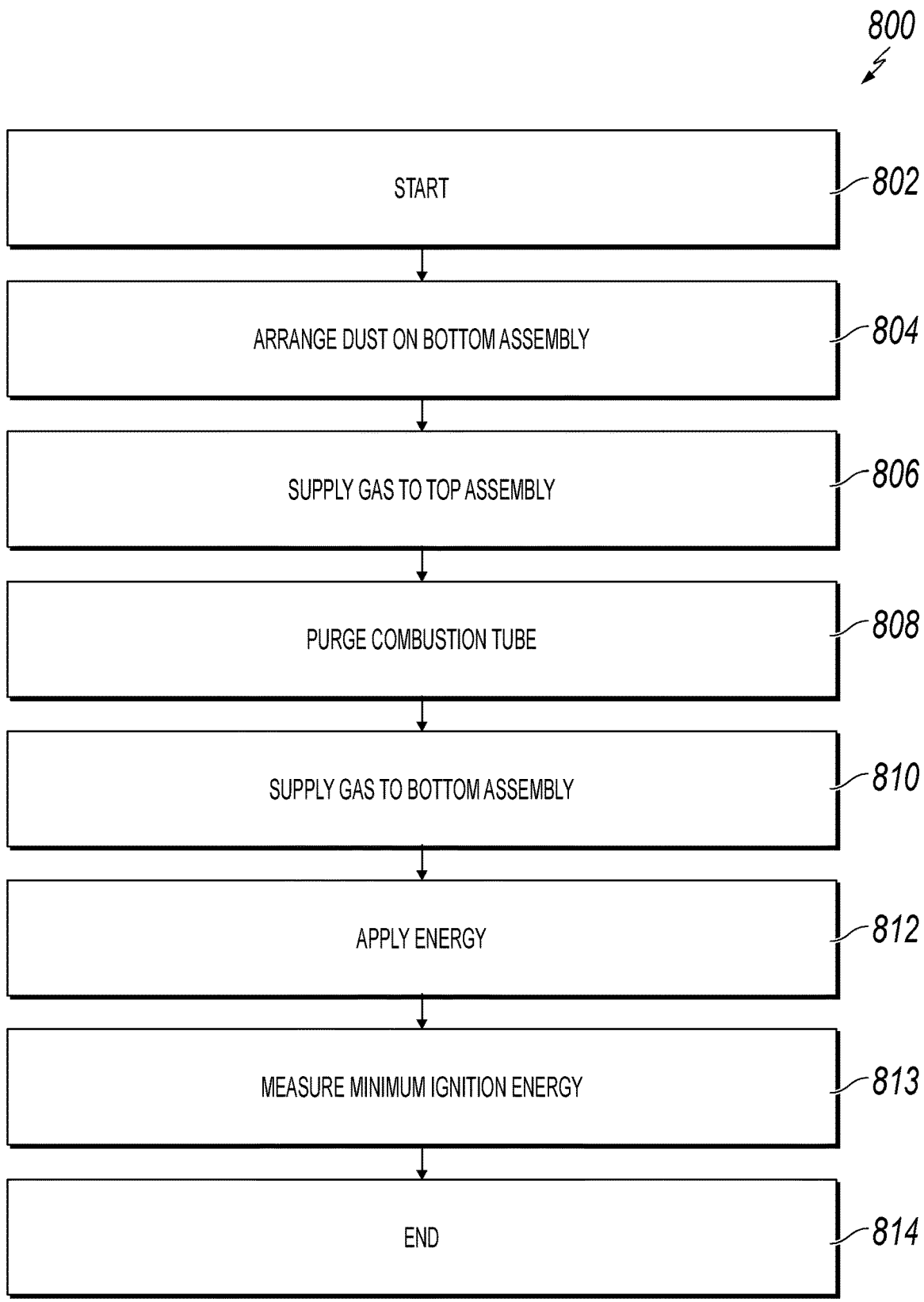
FIG. 8 is a flow diagram of a process for determining a minimum-ignition energy in accordance with an exemplary embodiment.

FIG. 8 is a flow diagram illustrating a process 800 for determining minimum-ignition energy. The process 800 begins at step 802. At step 804, a combustible dust is arranged on the bottom assembly 104 within the combustion tube 102. At step 806, the valve 114 is set to supply a gas from the gas source 110 to the top assembly 106. In various embodiments, the gas is an inerting gas such as, for example, nitrogen (N2); however, as will be discussed below, in other embodiments a flammable gas mixture may be utilized. At step 808, the combustion tube 102 is purged with the inerting gas from the gas source 110 through the top assembly 106. In a typical embodiment, the inerting gas is supplied to the combustion tube 102 at a rate of approximately 1 liter per minute for approximately 2 minutes. In a typical embodiment, the foam seal 204 and the flapper plate 202 prevent ingress of ambient air into the combustion tube 102 via the aperture 205. At step 810, the valve 114 is set to supply gas from the gas source 110 to the bottom assembly 104. Supply of gas to the bottom assembly causes the combustible dust to disperse in the combustion tube 102 in an, for example, aerosol manner. At step 812, incrementally increasing energy is applied to the interior of the combustion tube 102 via the ignition device 108 until combustion of the combustible dust is achieved. At step 813, the minimum ignition energy is measured. The process 800 ends at step 814.

Hybrid dust-gas explosions are dust explosions in which the atmosphere which the dust is dispersed my contain a portion of flammable gas. For such explosions, the hybrid MIE can be described as the lowest energy required to ignite this hybrid dust-gas cloud.

Utilization of the minimum ignition energy apparatus 100 and process 800 will lead to the generation of accurate hybrid MIE data. A significant difference between the hybrid MIE values measured with and without the minimum ignition energy apparatus 100 and process 800 are presented below.

While, partial inerting testing using the minimum-ignition-energy apparatus 100 has been demonstrated to lead to higher than expected MIE values; hybrid MIE testing using the minimum-ignition-energy apparatus 100 shows the MIE values reported in literature underestimated the hybrid MIE value, and are thus non-conservative. Therefore, the minimum-ignition-energy apparatus 100 leads to the correct MIE hybrid values ensuring the explosion risk is not underestimated.

As a proof of this concept, a historical standard for dust testing, Pulverized Pittsburgh Coal (PPC), has been tested in three methane-air atmospheres. Three pre-blended gas bottles were used for testing including; (1% methane, 99% air), (2% methane, 98% air) and (3% methane, 97% air). These three cylinders have a compositional variation equal or less than ±1%, and strictly adhered to the standards of <0.1 ppm carbon dioxide and <0.36 ppm moisture.

Figure 9:
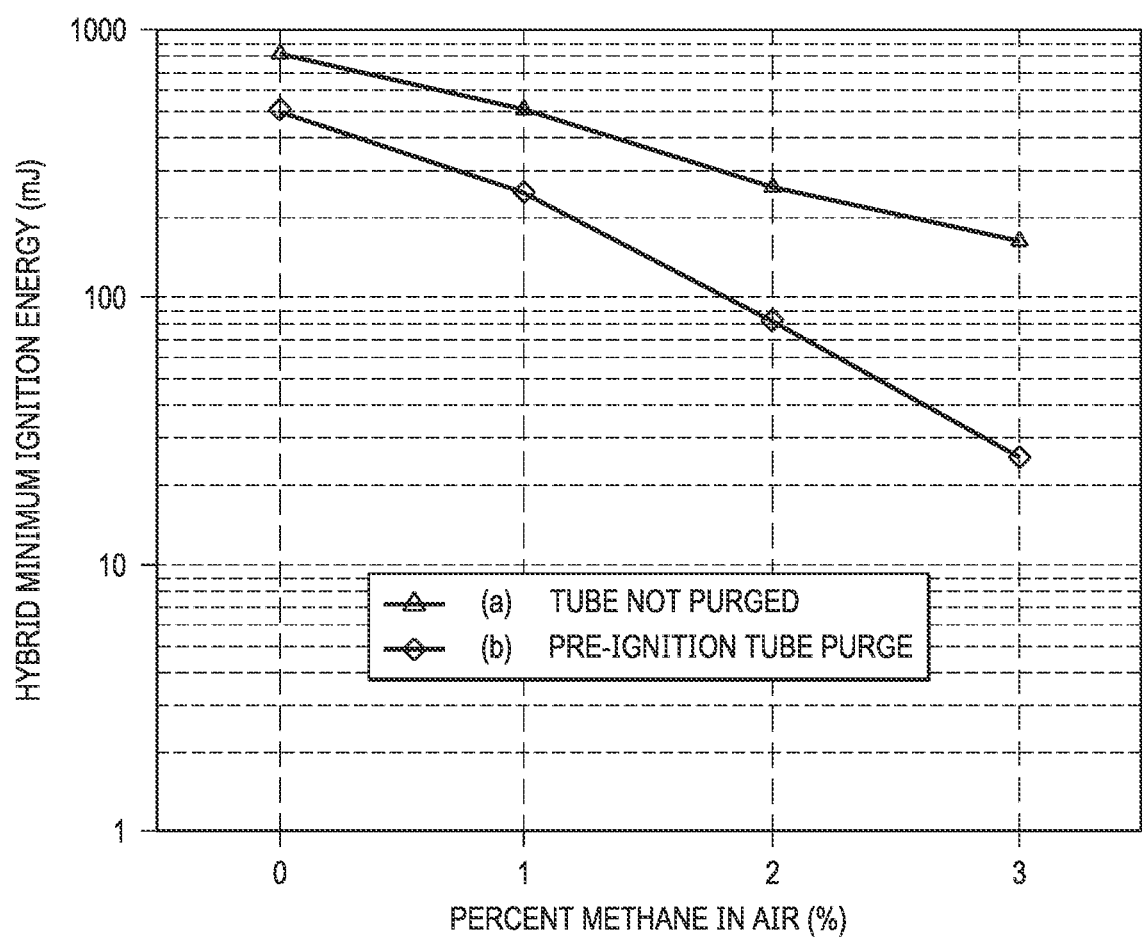
FIG. 9 is a graph illustrating Hybrid MIE for PPC-Methane-Air Mixtures.

Two distinct test procedures were executed. First, a typical historical approach found in existing literature; and second, the approach using the minimum-ignition-energy apparatus 100 and the process 800. The typical historical testing approach includes the following: 1) the dust is placed around the dispersion nozzle; 2) one of the above methane-air mixtures is connected to the minimum-ignition-energy apparatus 100 as described with respect to FIGS. 1-8 to provide a pulsed dispersion of the dust into the combustion tube 102; and 3) ignition of the hybrid dust cloud mixture is accomplished, for example, by spark discharge via the ignition device 108. FIG. 9 shows the variation in MIE for a PPC-methane-air hybrid system with volume percent methane in air. Case (a) represents the MIE values tested following standard procedure ASTM E2019-03 (2013) and that is typically reported in literature.

The second procedure utilizes the minimum-ignition-energy apparatus 100 and the process 800 and includes the following: 1) the dust is placed around the dispersion nozzle; 2) one of the above methane-air mixtures is passed through the second sparge plate 306 via the tube 310 and into the combustion tube 102 via the channel 312, thereby rendering the composition of the combustion tube 102 with the desired methane-air mixture prior to ignition; 3) the dust is dispersed with the same methane-air mixture as in step 2; and 4) ignition of the hybrid dust cloud mixture is accomplished, for example, by spark discharge via the ignition device 108. The results of this method are shown in FIG. 9, case (b).

Comparison of the hybrid MIE values for case (a) and case (b) at every concentration of methane, demonstrates that the hybrid MIE in case (b) is lower than that in case (a), which indicates that the second method of tube sparging significantly decreases the hybrid MIE value.

The difference in the hybrid MIE values between case (a) and case (b) further proves the significance of the device modifications and implementation of improved test methods. The hybrid MIE values from the minimum-ignition-energy apparatus 100 are more accurate and lower than those reported in literature.

Until now, various studies on hybrid dust explosions have not considered the effect of pre-purging the combustion tube 102 on the measured MIE values. For several decades, hybrid MIE testing has been done incorrectly and the reported values are non-conservative. This discrepancy in values can be misleading and can prove hazardous in industrial facilities. Therefore, the minimum ignition energy apparatus 100 is meaningful and of great utility for hybrid MIE testing as it enables more accurate measurements. This invention is significant for industries for the prevention of major dust explosion incidents.

Although various embodiments of the method and system of the present disclosure have been illustrated in the accompanying Drawings and described in the foregoing Specification, it will be understood that the disclosure is not limited to the embodiments discussed herein, but is capable of numerous rearrangements, modifications, and substitutions without departing from the spirit and scope of the disclosure as set forth herein. It is intended that the Specification and examples be considered as illustrative only.

What is claimed is:

1. A minimum-ignition-energy testing apparatus comprising:
  a combustion tube;
  an ignition device exposed to an interior of the combustion tube;
  a bottom assembly coupled to a lower end of the combustion tube;
  a top assembly coupled to an upper end of the combustion tube, the top assembly comprising:
  a first sparge plate, the first sparge plate having a first aperture formed therein;
  a second sparge plate coupled the first sparge plate, the second sparge plate having formed therein a second aperture that aligns in registry with the first aperture;
  a channel formed in the second sparge plate about a perimeter of the second aperture, the channel having a plurality of holes disposed therein, the holes being formed through a thickness of the second sparge plate; and
  a tube formed through in the second sparge plate, the tube fluidly coupling the channel to a gas source.

2. The minimum-ignition-energy testing apparatus of claim 1, wherein the ignition device is a spark ignition device.

3. The minimum-ignition-energy testing apparatus of claim 1, comprising the gas source fluidly coupled to at least one of the bottom assembly and the top assembly.

4. The minimum-ignition-energy testing apparatus of claim 1, comprising a flow meter fluidly coupled to the gas source.

5. The minimum-ignition-energy testing apparatus of claim 1, wherein the top assembly comprises a flapper plate hingedly moveable between an open position and a closed position.

6. The minimum-ignition-energy testing apparatus of claim 5, comprising a foam seal disposed between the flapper plate about a perimeter of the first aperture.

7. The minimum-ignition-energy testing apparatus of claim 1, wherein the first sparge plate and the second sparge plate are constructed of 316 stainless steel.

8. A minimum-ignition-energy testing method comprising:
- placing a material on a bottom assembly of a minimum-ignition-energy testing apparatus;
- enclosing the material in a combustion tube;
- providing a gas to a top assembly coupled to the combustion tube to purge the combustion tube, the gas being provided to a channel formed in the top assembly, the channel being formed about a perimeter of an aperture formed in the top assembly, the gas being provided to the combustion tube via a plurality of holes formed in a sparge plate of the top assembly and fluidly coupled to the channel;
- dispersing the material into the combustion tube;
- applying an ignition energy to the combustion tube; and
- measuring the minimum ignition energy.

9. The method of claim 8, wherein the gas is an inerting gas.

10. The method of claim 9, wherein the inerting gas is nitrogen.

11. The method of claim 8, wherein the gas is a mixture containing a flammable gas.

12. The method of claim 11, wherein the flammable gas is methane.

13. The method of claim 8, wherein the material is a combustible dust.

14. The method of claim 8, wherein the dispersing comprises applying the gas to the bottom assembly.

15. The method of claim 8, wherein the applying an ignition energy comprises applying a spark.

16. A top assembly, the top assembly comprising:
- a top base plate having a first aperture formed therein and a flapper plate pivotably coupled thereto, the flapper plate covering the first aperture;
- a first sparge plate coupled to the top base plate, the first sparge plate having a second aperture formed therein that aligns in registry with the first aperture;
- a second sparge plate coupled the first sparge plate, the second sparge plate having formed therein a third aperture that aligns in registry with the first aperture and with the second aperture;
- a channel formed in the second sparge plate about a perimeter of the third aperture, the channel having a plurality of holes disposed therein, the holes being formed through a thickness of the second sparge plate; and
- a tube formed through in the second sparge plate, the tube fluidly coupling the channel to a gas source.

17. The top assembly of claim 16, wherein the top assembly comprises a flapper plate hingedly moveable between an open position and a closed position.

18. The top assembly of claim 16, wherein the first sparge plate and the second sparge plate are constructed of 316 stainless steel.

19. The top assembly of claim 16, comprising a foam seal disposed between the flapper plate about a perimeter of the first aperture.

* * * * *